United States Patent
Dukat et al.

(10) Patent No.: US 7,074,304 B2
(45) Date of Patent: Jul. 11, 2006

(54) PROCESS FOR PURIFYING ALICYCLIC ALCOHOLS

(75) Inventors: Wolfgang Dukat, Oberhausen (DE); Peter Lappe, Dinslaken (DE); Klaus Schmid, Dinslaken (DE); Horst Scholz, Dinslaken (DE); Edgar Storm, Oberhausen (DE)

(73) Assignee: Celanese Chemicals Europe GmbH (DE)

( * ) Notice: Subject to any disclaimer, the term of this patent is extended or adjusted under 35 U.S.C. 154(b) by 84 days.

(21) Appl. No.: 10/318,564

(22) Filed: Dec. 13, 2002

(65) Prior Publication Data

US 2003/0183502 A1    Oct. 2, 2003

(30) Foreign Application Priority Data

Dec. 14, 2001 (DE) ................ 101 61 597

(51) Int. Cl.
*B01D 3/34* (2006.01)
*C07C 29/80* (2006.01)

(52) U.S. Cl. .............. 203/61; 203/6; 203/34; 203/35; 203/41; 568/700

(58) Field of Classification Search ............... 203/61, 203/34, 57, 6, 35, 41; 568/817, 820, 700, 568/708, 724, 719; 585/800
See application file for complete search history.

(56) References Cited

U.S. PATENT DOCUMENTS

| 2,889,385 | A |   | 6/1959  | Gilbert et al. |
|-----------|---|---|---------|----------------|
| 2,909,458 | A | * | 10/1959 | Richter ................ 514/510 |
| 2,984,643 | A | * | 5/1961  | Gunther et al. ............... 525/41 |
| 3,384,672 | A | * | 5/1968  | Illingworth ................ 568/837 |
| 3,990,952 | A |   | 11/1976 | Katzen et al. |
| 4,306,943 | A | * | 12/1981 | Mori et al. ................... 203/29 |
| 4,383,893 | A | * | 5/1983  | Kaibel et al. ................ 203/35 |
| 5,264,638 | A |   | 11/1993 | Nilubol |
| 5,354,911 | A | * | 10/1994 | Weber et al. ............... 568/691 |
| 6,051,743 | A | * | 4/2000  | Bahrmann et al. ........... 568/882 |
| 6,093,845 | A | * | 7/2000  | van Acker et al. .......... 560/239 |
| 6,117,277 | A | * | 9/2000  | Zgorzelski et al. ........... 203/37 |

FOREIGN PATENT DOCUMENTS

| DE | 42 26 282     |   | 2/1994 |
| EP | 0 378 756     |   | 7/1990 |
| EP | PCT/EP96/0063 |   | 2/1996 |
| JP | 2000219654    | * | 8/2000 |

OTHER PUBLICATIONS

XP-002253295 & JP 2001 131105 A, May 15, 2001, Daicel Chem. Ind. Ltd. 2 pages.

* cited by examiner

*Primary Examiner*—Virginia Manoharan
(74) *Attorney, Agent, or Firm*—Charles A. Muserlian

(57) ABSTRACT

A process for purifying alicyclic alcohols by distillation, wherein the alicyclic alcohols are distilled in the presence of from 1 to 550 ppm of acidic compounds.

8 Claims, No Drawings

PROCESS FOR PURIFYING ALICYCLIC ALCOHOLS

The present invention relates to a process for purifying alicyclic alcohols by distillation in the presence of acidic compounds.

STATE OF THE ART

Alicyclic alcohols are based on monocyclic or polycyclic aliphatic hydrocarbons which bear one or more hydroxyl groups.

Alicyclic alcohols are of great economic importance. They are used widely in the synthesis of alkyd resins, polyesters, polyacrylates or polycarbonates for surface coatings, paints or adhesives, as is known, for example, from DE-A-1 916 287.

These alicyclic alcohols are preferably prepared by hydroformylation of monocyclic or polycyclic olefins with subsequent hydrogenation of the aldehydes formed as intermediates. A review may be found, for example, in J. Falbe, Synthesen mit Kohlenmonoxid, Springer Verlag Berlin 1967, p. 34 ff, Cornils, Chemiker Zeitung, volume 98, 1974, page 70 ff, or in J. Falbe and N. Huppes, Brennstoffchemie 48 (1967), 182.

Important alicyclic alcohols are derived from dicyclopentadiene (tricyclo-[5.2.1.0$^{2,6}$]deca-3,8-diene). Hydroformylation of this starting olefin and subsequent hydrogenation provides a route to the tricyclodecane alcohols which are frequently referred to as TCD alcohols in the prior art. Examples of such TCD alcohols are TCD alcohol DM (isomer mixture comprising 3(4),8(9)-bis(hydroxymethyl)tricyclo[5.2.1.0$^{2,6}$]decane) and TCD alcohol OM (isomer mixture comprising 8(9)-hydroxy-3(4)-hydroxymethyltricyclo-[5.2.1.0$^{2,6}$]decane) which is obtainable by hydroformylation of TCD alcohol E (8(9)-hydroxytricyclo[5.2.1.0$^{2,6}$]dec-3-ene) as described in DE-B-1 018 415. In the case of the designation of the isomer mixture as 3(4),8(9)-bis(hydroxymethyl)tricyclo[5.2.1.0$^{2,6}$]decane, one hydroxymethyl radical bound to the tricyclodecane skeleton is located in the 3 to 4 position and the other hydroxymethyl radical is located in the 8 or 9 position.

Accordingly, the designation 3(4),8(9)-bis(hydroxymethyl)tricyclo[5.2.1.0$^{2,6}$]-decane refers to a mixture comprising 3,8-bis(hydroxymethyl)tricyclo-[5.2.1.0$^{2,6}$]decane, 3,9-bis(hydroxymethyl)tricyclo[5.2.1.$^{2,6}$]decane, 4,8-bis(hydroxymethyl)tricyclo[5.2.1.0$^{2,6}$]decane and 4,9-bis(hydroxymethyl)tricyclo[5.2.1.0$^{2,6}$[decane and the designation 8(9)-hydroxy-3(4)-hydroxy-3-hydroxymethyltricyclo[5.2.1.0$^{2,6}$]decane, 9-hydroxy-3-hydroxymethyltricyclo[5.2.1.0$^{2,6}$]decane, 8-hydroxy-4-hydroxymethyltricyclo[5.2.1.0$^{2,6}$]-decane and 9-hydroxy-4-hydroxymethyltricyclo[5.2.1.0$^{2,6}$]decane.

Further alicyclic alcohols are obtained by the rhodium-catalyzed hydroformylation reaction of tricyclopentadiene (isomer mixture comprising 3a,4,4a,5,8,8a,9,9a-octahydro-4,9:5,8-dimethanobenz[f]indene and 1,4,4a,4b,5,8,8a,9a-octahydro-1,4:5,8-dimethanofluorene) as described in EP-A1-1 065 194 and subsequent hydrogenation to form the alcohols. This reaction forms the PCPD alcohol DM, which is an isomer mixture comprising 1,4:5,8-dimethano-2(3),6(7)-bis(hydroxymethyl)perhydrofluorene and 4,9:5,8-dimethano-1(2),6(7)-bis(hydroxymethyl)perhydrobenz[f]indene.

The designation 1,4:5,8-dimethano-2(3),6(7)-bis-(hydroxymethyl)perhydrofluorene refers to a mixture comprising 1,4:5,8-dimethano-2,6-bis(hydroxy-methyl)perhydrofluorene,1,4:5,8-dimethano-2,7-bis(hydroxymethyl) perhydrofluorene, 1,4:5,8-dimethano-3,6-bis(hydroxymethyl)perhydrofluorene and 1,4:5,8-dimethano-3,7-bis(hydroxymethyl)perhydrofluorene and the designation 4,9:5,8-dimethano-1(2),6(7)-bis(hydroxymethyl)perhydrobenz[f]indenerefers to a mixture comprising 4,9:5,8-dimethano-1,6-bis-(hydroxymethyl)perhydrobenz[f]indene, 4,9:5,8-dimethano-2,6-bis(hydroxymethy)perhydrobenz[f]indene, 4,9:5,8-dimethano-1,7-bis(hydroxymethyl)perhydrobenz[f]indene and 4,9:5,8-dimethano-2,7-bis(hydroxymethyl)perhydrobenz[f]indene.

A further important alicyclic alcohol is BCH alcohol M, an isomer mixture comprising 2-hydroxymethylbicyclo[2.2.1]heptane.

For many applications, for example in the preparation of esters of acrylic acid, the use of highly pure alcohols is absolutely necessary in order to keep adverse effects of esterification or polycondensation reactions as small as possible. The use of highly pure alcohols is also necessary to avoid the formation of undesirably colored products. Thus, compounds containing aldehyde groups are particularly troublesome impurities.

In the industrial preparation of alicyclic alcohols via the hydroformylation of the corresponding olefins and subsequent hydrogenation, the desired alicyclic alcohols always contain traces of incompletely hydrogenated compounds having one or more aldehyde groups. For example, industrially available TCD alcohol DM contains small amounts of TCD hydroxy-aldehyde or TCD dialdehyde. The determination of the impurities containing aldehyde groups is generally carried out in accordance with DIN 53173, issue 1983-02. Their content is reported as carbonyl number, also referred to as CO number, in mg of KOH/g. In technical-grade TCD alcohol DM, the carbonyl number is generally in a range of 0.2–0.8 mg of KOH/g, corresponding to a TCD hydroxyaldehyde content of 0.07–0.28% by weight.

The compounds containing aldehyde groups frequently display a boiling behavior similar to the fully hydrogenated alcohols, so that simple single-stage distillation does not lead to high-purity alicyclic alcohols. The purification has hitherto invariably been carried out by means of a multi-stage fractional distillation employing a large number of theoretical plates. In this, the alicyclic alcohols are subjected to thermal stress for a number of hours, with bottom temperatures of from 100 to 240° C. generally being employed. The increase in the separation performance of the distillation leads to considerable product losses caused by decomposition of light and intermediate fractions and by the formation of high boilers. Furthermore, there is a risk of some aldehyde formation even during the distillation of the crude alcohols due to the thermal stress of the crude alcohols.

Processes for purifying oxo alcohols by distillation with addition basic compounds are known from the prior art. IN the process disclosed in U.S. Pat. No. 2,889,375, alkaline earth metal compounds, in particular oxides, hydroxides or carbonates, are added in an amount of 1% by weight, based on the amount of feed, to aliphatic, acyclic oxo alcohols containing small amounts of aldehydes in the bottom of the column. According to EP-B-0 869 936, aliphatic alcohols can be purified by distillation in the presence of small amounts of alkali metal hydroxide. This and other objects and advantages of the invention will become obvious from the following detailed description.

OBJECTS OF THE INVENTION

It is an object of the invention to provide a process for the distillation of alicyclic alcohols which makes it possible to separate off impurities containing aldehyde groups in a simple and inexpensive manner and also suppresses the formation of such compounds during the thermal stress involved in the distillation.

THE INVENTION

It has now surprisingly been found that the addition of small amounts of acidic compounds during the distillation of alicyclic alcohols enables residual aldehydes present to be eliminated and suppresses the formation of corresponding aldehydes.

The present invention accordingly provides a process for purifying alicyclic alcohols by distillation. In this process, the alicyclic alcohols are distilled in the presence of from 1 to 500 ppm of acidic compounds, based on the amount of alicyclic alcohol used.

When the process of the invention is employed, a simple distillation bridge having only one theoretical plate suffices to obtain the desired alicyclic alcohols in a very high purity. In general, the carbonyl numbers of the distillates obtained are less than 0.05 mg of KOH/g. Since, in contrast to the prior art, no complicated column arrangements having many theoretical plates is necessary but instead, surprisingly, only a simple distillation bridge having only one theoretical plate is sufficient, high distillation yields of the desired pure alcohols are advantageously obtained and only small distillation losses have to be accepted. In general, the distillation yield is above 98% of the feed material.

The alicyclic alcohols are monohydric or polyhydric alcohols which are based on monocyclic or polycyclic aliphatic hydrocarbons and generally have from 7 to 17 carbon atoms in the molecule. Alicyclic alcohols to which the process of the invention can be applied particularly successfully are TCD alcohol DM and TCD alcohol OM.

The acidic compound which can be added to the process of the invention are subject to no restriction and it is possible to add all acidic compounds with which those skilled in the art are familiar as long as the acidic compounds added have a sufficiently high boiling point or sublimation point to ensure that no acidic compounds get into the distillate. Preference is given to using acidic compounds which are solid at room temperature. Particularly useful acidic compounds are aliphatic or aromatic sulfonic acids which bear one or more sulfonic groups. Examples of suitable sulfonic acids are para-toluenesulfonic acid, naphthalenesulfonic acid, sulfanilic acid and camphorsulfonic acid. The acid salts of strong or weak mineral acids, for example potassium hydrogen sulfate, sodium dihydrogen phosphate, the strong or weak mineral acids themselves, e.g. sulfuric acid or phosphoric acid, are also suitable, as are tetraalkylammonium salts of strong and weak mineral acids, e.g. tetrabutylammonium hydrogen sulfate.

Furthermore, solid nonmetal oxides, e.g. diphosphorus pentoxide, or ion exchangers which have been converted into the acid form can also be used successfully. High-boiling aliphatic or aromatic, monobasic or polybasic carboxylic acids, for example 9-anthracenecarboxylic acid, thapsic acid or trimellitic acid, are also suitable for use in the process of the invention, although the use of sulfonic acids is preferred. It has been found to be particularly advantageous to use para-toluenesulfonic acid, camphorsulfonic acid or potassium hydrogen sulfate.

The amount of acidic compound added is in the range of 1–500 ppm, preferably in the range of 5–250 ppm and particularly preferably in the range of 5–50 ppm, in each case based on the amount of alicyclic alcohol used. Additions of smaller amounts no longer display a satisfactory effect. Additions of larger amounts are likewise not advisable, since they unnecessarily increase the cost of the process, increase the amount of extraneous material present and can lead to secondary reactions such as ether formation and ester formation. The acidic compounds are advantageously added in pure form as liquid or as solid, preferably as solid, to the crude alcohol.

It is sufficient to use a simple distillation bridge having only one theoretical plate for the purification by distillation. However, the use of distillation columns is not ruled out, although higher distillation losses have to be expected when they are used. If distillation columns are employed, they generally have from 2 to 40 trays. The pressure and temperature conditions have to be matched individually to the alcohols to be purified.

As the following examples show, the work-up of alicyclic alcohols by distillation in the presence of small amounts of acidic compounds u;sing a simple distillation bridge can give alcohols whose carbonyl number has been reduced to generally below 10%, frequently below 5%, of the initial value in the feed alcohol. Since a simple distillation bridge having only one theoretical plate is sufficient for the distillation, only small distillation losses are observed in the process of the invention.

The following examples illustrate the invention without restricting it to particular embodiments.

COMPARATIVE EXAMPLE 1

1860.1 g of TCD alcohol DM (carbonyl number: 0.57 mg of KOH/g) were placed in 4 l round-bottom flask equipped with thermometer and Claisen bridge and were purged with nitrogen for 30 minutes while stirring at a temperature of 80° C. At a temperature at the top of 172–176° C. and a pressure of 2 mbar, 1796.0 g of TCD alcohol DM having a carbonyl number of 0.54 mg of KOG/g were obtained. This corresponded to a distillation yield of 96.6%. The carbonyl number was reduced only insignificantly to 94.0% of the initial value.

COMPARATIVE EXAMPLE 2

1604.8 g of TCD alcohol DM (carbonyl number: 0.22 mg of KOH/g) were placed in a 4 l round bottom flask equipped with thermometer and a packed column having 4.5 theoretical plates and were purged with nitrogen for 30 minutes while stirring at a temperature of 80° C. After a first fraction amounting to 410.9 g (25.6% of the initial weight) had been obtained, 1139.6 g of TCD alcohol DM having a carbonyl number of 0.041 mg of KOH/g were obtained at a temperature at the top of 175° C. and a pressure of 2 mbar. This corresponded to a distillation yield of 71.0%. The carbonyl number was reduced to 18.5% of the original value.

EXAMPLE 1

1923.4 g of TCD alcohol DM (carbonyl number: 0.57 mg of KOH/g) were placed in a 4 l round-bottom flask equipped with thermometer and Claisen bridge, admixed with 19.2 mg of para-toluenesulfonic acid and purged with nitrogen for 30 minutes while stirring at a temperature of 80° C. At a temperature at the top of 172–176° C. and a pressure of 2 mbar, 1908.4 g of TCD alcohol DM having a carbonyl number of 0.036 mg of KOH/g were obtained. This corresponded to a distillation yield of 99.2% The carbonyl number had been reduced to 6.4% of the original value.

EXAMPLE 2

Using the procedure described in example 1, 1964.9 g of TCD alcohol DM (carbonyl number: 0.57 mg of KOH/g) were admixed with 98.3 mg of paratoluenesulfonic acid. The subsequent distillation gave 1928.4 g of TCD alcohol DM having a carbonyl number of 0.038 mg of KOH/g. This corresponded to a distillation yield of 98.1%. The carbonyl number had been reduced to 6.6% of the original value.

EXAMPLE 3

Using the procedure described in example 1, 1938.0 g of TCD alcohol DM (carbonyl number: 0.57 mg of KOH/g) were admixed with 193.8 mg of paratoluenesulfonic acid. The subsequent distillation gave 1897.2 g of TCD alcohol DM having a carbonyl number of 0.065 mg of KOH/g. This corresponded to a distillation yield of 97.9%. The carbonyl number had been reduced to 11.4% of the original value.

EXAMPLE 4

Using the procedure described in example 1, 1803.5 g of TCD alcohol DM (carbonyl number: 0.81 mg of KOH/g) were admixed with 9.0 mg of paratoluenesulfonic acid. The subsequent distillation gave 1775.5 g of TCD alcohol DM having a carbonyl number of 0.053 mg of KOH/g. This corresponded to a distillation yield of 98.5%. The carbonyl number had been reduced to 6.6% of the original value.

EXAMPLE 5

Using the procedure described in example 1, 1866.0 g of TCD alcohol DM (carbonyl number 0.81 mg of KOH/g) were admixed with 18.7 mg of paratoluenesulfonic acid. The subsequent distillation gave 1853.3 g of TCD alcohol DM having a carbonyl number of 0.050 mg of KOH/g. This corresponded to a distillation yield of 99.3%. The carbonyl number had been reduced to 6.2% of the original value.

EXAMPLE 6

Using the procedure described in example 1, 1967.5 g of TCD alcohol DM (carbonyl number: 0.81 mg of KOH/g) were admixed with 196.8 mg of paratoluenesulfonic acid. The subsequent distillation gave 1928.7 g of TCD alcohol DM having a carbonyl number of 0.032 mg of KOH/g. This corresponded to a distillation yield of 98.0%. The carbonyl number had been reduced to 4.0% of the original value.

EXAMPLE 7

Using the procedure described in example 1, 1936.5 g of TCD alcohol DM (carbonyl number: 0.57 mg of KOH/g) were admixed with 19.4 mg of camphorsulfonic acid. The subsequent distillation gave 1918.5 g of TCD alcohol DM having a carbonyl number of 0.045 mg of KOH/g. This corresponded to a distillation yield of 99.1%. The carbonyl number had been reduced to 7.8% of the original value.

EXAMPLE 8

Using the procedure described in example 1, 1854.5 g of TCD alcohol DM (carbonyl number: 0.57 mg of KOH/g) were admixed with 94.4 mg of camphorsulfonic acid. The subsequent distillation gave 1836.8 g of TCD alcohol DM having a carbonyl number of 0.052 mg of KOH/g. This corresponded to a distillation yield of 98.2%. The carbonyl number had been reduced to 9.1% of the original value.

EXAMPLE 9

Using the procedure described in example 1, 1968.6 g of TCD alcohol DM (carbonyl number: 0.57 mg of KOH/g) were admixed with 196.9 mg of camphorsulfonic acid. The subsequent distillation gave 1926.3 g of TCD alcohol DM having a carbonyl number of 0.074 mg of KOH/g. This corresponded to a distillation yield of 97.9%. The carbonyl number had been reduced to 13.1% of the original value.

EXAMPLE 10

Using the procedure described in example 1, 2048.6 g of TCD alcohol DM (carbonyl number: 1.17 mg of KOH/g) were admixed with 102.4 mg of potassium hydrogen sulfate. The subsequent distillation gave 2025.4 g of TCD alcohol DM having a carbonyl number of 0.055 mg of KOH/g. This corresponded to a distillation yield of 98.9%. The carbonyl number had been reduced to 4.7% of the original value.

EXAMPLE 11

Using the procedure described in example 1, 1888.1 g of TCD alcohol DM (carbonyl number: 1.17 mg of KOH/g) were admixed with 150 mg of 9-anthracenecarboxylic acid. The subsequent distillation gave 1869.5 g of TCD alcohol DM having a carbonyl number of 0.69 mg of KOH/g. This corresponded to a distillation yield of 99.0%. The carbonyl number had been reduced to 59.0% of the original value.

What we claim is:

1. A process for purifying alicyclic alcohols by distillation, as the top product consisting of distilling the alicyclic alcohols in the presence of from 1 to 500 ppm of acidic compounds, based on the amount of the alicyclic alcohol used.

2. The process as claimed in claim 1, wherein the alicyclic alcohols have from 7 to 17 carbon atoms in the molecule.

3. The process as claimed in claim 1 wherein acidic compounds used are selected from the group consisting of aliphatic or aromatic sulfonic acids, aliphatic or aromatic monobasic or polybasic carboxylic acids, acid salts of strong or weak mineral acids, strong or weak mineral acids, tetraalkylammonium salts of strong or weak mineral acids, solid nonmetal oxides and acidic ion exchangers.

4. The process of claim 1 wherein the acidic compound used is selected from the group consisting of paratoluenesulfonic acid, naphthalene-sulfonic acid, sulfanilic acid, camphorsulfonic acid, potassium hydrogen sulfate, sodium dihydrogen phosphate, tetrabutyl-ammonium hydrogen sulfate, 9-anthracene-carboxylic acid and diphosphorous pentoxide.

5. The process as claimed in claim 1 wherein the acidic compounds are added in an amount of 5–250 ppm, based on the amount of the alicyclic alcohol.

6. The process as claimed in claim 1 wherein the distillation is carried out at a temperature of from 100 to 240°C.

7. The process of claim 1 wherein the acidic compounds are added in an amount of 5 to 50 ppm based on the amount of the alicyclic alcohol.

8. A process for purifying alicyclic alcohols by distillation as the top product wherein the alicyclic alcohol used is an isomer mixture selected from the group consisting of 3,8-bis(hydroxymethyl)tricyclo[5.2.1.0$^{2,6}$]decane, 3,9-bis(hydroxymethyl)tricyclo[5.2.1.0$^{2,6}$]decane, 4,8-bis(hydroxymethyl)tricyclo[5.2.1.0$^{2,6}$]decane) and 4,9-bis(hydroxymethyl)tricyclo[5.2.1.0$^{2,6}$]decane, an isomer mixture of 8-hydroxymethyltricyclo[5.2.1.0$^{2,6}$]decane, 9-hydroxy-3-hydroxymethyltricyclo[5.2.1.0$^{2,6}$]decane, 8-hydroxy-4-hydroxymethyltricyclo[5.2.1.0$^{2,6}$]decane and 9-hydroxy-4-hydroxy-methltricyclo[5.2.1.0$^{2,6}$]decane, an isomer mixture of 1,4:5,8-dimethano-2,6-bis(hydroxymethyl)perhydrofluorene, 1,4:5,8-dimethano-2,7-bis(hydroxymethyl)perhydrofluorene and 1,4:5,8-dimethano-3,6-bis(hydroxymethyl)perhydrofluorene and 1,4:5,8-dimethano-3,7-bis(hydroxymethyl)perhydrofluorene, and 4,9:5,8-dimethano-1,6-bis(hydromethyl)perhydrobenz[f]idene, 4,9:5,8-dimethano-2,6-bis(hydroxymethyl)perhydrobenz[f]idene, 4,9:5,8-dimethano-2,7-bis(hydroxymethyl)perhydrobenz[f]idene and 4,9:5,8-dimethano-2,7-bis(hydroxymethyl)perhydrobenz[f]idene and an isomer mixture of 2-hydroxymethylbicyclo[2.2.1]heptane consisting of distilling the alicyclic alcohols in the presence of from 1 to 500 ppm of acidic compounds, based on the amount of the alicyclic alcohol used.

* * * * *